United States Patent [19]

Toy

[11] Patent Number: 5,571,501
[45] Date of Patent: Nov. 5, 1996

[54] ANTIBACTERIAL ORAL CARE COMPOSITION CONTAINING TRICLOSAN OF IMPROVED COMPATIBILITY

[75] Inventor: Arthur Toy, Stanford, Conn.

[73] Assignee: Colgate Palmolive Company, New York, N.Y.

[21] Appl. No.: 213,279

[22] Filed: Mar. 15, 1994

[51] Int. Cl.$^6$ .......................... A61K 7/16; A61K 31/085
[52] U.S. Cl. .......................... 424/49; 514/721; 568/637; 424/57; 510/116; 510/386; 510/388
[58] Field of Search ........................ 424/49–58; 514/721; 568/639; 252/106

[56] References Cited

U.S. PATENT DOCUMENTS

| | | | |
|---|---|---|---|
| 4,010,252 | 3/1977 | Hewitt | 424/47 |
| 5,087,444 | 2/1992 | Jackson et al. | 424/49 |
| 5,240,697 | 8/1993 | Norfleet et al. | 424/52 |
| 5,290,541 | 3/1994 | Liang | 424/49 |

OTHER PUBLICATIONS

15 Jun. 1990 Commission of European Communities, Annex, $C_{12}H_7Cl_3O_2$.K, Phenol, 5–Chloro–2–(2,4–dichlorophenoxy)–, potassium salt, RN 94087–36–2, EIN 301–930.2.

Caseino, C.A. 110: 160260c of E.P. 278744 (Aug. 17, 1988) (Triclosan and $K^+$ for desensitizing hypersensitive teeth) (Toothpaste, KNO3, triclosan).

Hewitt C.A. 87: 29009s of U.S. Pat. No. 4,010,252 (Mar. 1, 1977) (Colgate Palmolive) (Antimicrobial compositions–the product resulting from the combination of Triclosan, KOH).

"Triclosan" Triclosan Phosphate Triclosan Salts Triclosan Esters 21 Apr. 1994 Chem. Abstracts Index Name, Other Names Structure On Line Search Printout.

*Primary Examiner*—Shep K. Rose
*Attorney, Agent, or Firm*—Paul Shapiro

[57] ABSTRACT

An aqueous based dentifrice containing the potassium salt of 2,4,4'-trichloro-2'-hydroxy-diphenyl ether (Triclosan).

6 Claims, No Drawings

ANTIBACTERIAL ORAL CARE COMPOSITION CONTAINING TRICLOSAN OF IMPROVED COMPATIBILITY

BACKGROUND OF THE INVENTION

1. Field of the Invention

This invention relates to an antibacterial oral composition such as a mouthrinse or dentifrice and more particularly to an oral composition containing as the antibacterial agent a Triclosan salt having improved compatibility with the ingredients of the oral composition.

2. The Prior Art

It is known in the art, e.g. U.S. Pat. No. 4,894,220, U.S. Pat. No. 5,032,386, that 2,4,4'-trichloro-2'-hydroxy-diphenyl ether (referred to hereinafter by its international non-proprietary name Triclosan) is a substantially water-insoluble non-cationic antibacterial agent which when properly dispersed in aqueous based oral compositions functions as an antiplaque agent.

It is further known to the art to incorporate potassium salts in oral compositions for tartar control and desensitization of teeth. U.S. Pat. Nos. 4,51 5,772, 4,590,066, 4,684,518, 4,806,339 disclose the use of alkali metal pyrophosphate salts such as potassium pyrophosphate in combination with soluble fluorides as antitartar agents. U.S. Pat. No. 3,863,006, discloses that nitrates, such as potassium nitrate, when incorporated in aqueous solutions used as mouthrinses or in dentifrices such as toothpastes, desensitizes sensitive teeth. European Patent 0278744 discloses a dentifrice composition for desensitizing sensitive teeth which contains a combination of Triclosan and potassium salts such as potassium nitrate or potassium citrate.

One of the drawbacks to the use of Triclosan in aqueous based mouthrinses or dentifrices is that Triclosan is only very slightly soluble. Triclosan becomes even more insoluble in the presence of water soluble potassium salts such as potassium nitrate or potassium citrate and other metal desensitizing salts as well as metal antitartar salts, thereby materially reducing the efficacy of the Triclosan.

Accordingly it is the object of the present invention to provide an improved dentifrice composition which overcomes the incompatibility of Triclosan with potassium salts incorporated in oral compositons.

SUMMARY OF THE INVENTION

In accordance with the present invention there is provided an aqueous based oral composition comprising an orally acceptable vehicle for such composition, an inorganic potassium salt and an effective antibacterial amount of the potassium salt of Triclosan.

It has been found that Triclosan, being a substituted phenol, is acidic. It can form a potassium salt. By forming the potassium salt of Triclosan prior to its addition to an aqueous based oral care composition containing inorganic potassium salts, such as potassium nitrate or potassium pyrophosphate, the potassium salt of Triclosan exhibits improved compatibility with these potassium salts.

Although Triclosan and inorganic potassium salts such as potassium nitrate have been suggested as desensitizing components of oral compositions, oral compositions which contain Triclosan and potassium ion combined in one compound are believed to be novel and not suggested by the prior art for improving the compatibility of Triclosan in aqueous based oral compositions. The potassium salt of Triclosan is compatible with other potassium salts in the oral composition such as desensitizing salt such as potassium nitrate and antitartar salts such as potassium pyrophosphate whereby loss of Triclosan during storage and before use is avoided, which loss would otherwise cause a decrease in the antibacterial action attributable to the presence of the Triclosan in the oral composition.

DESCRIPTION OF THE PREFERRED EMBODIMENTS

The potassium salt of Triclosan of the present invention is prepared by reacting the acidic hydroxy group in the 2' position of the molecule with potassium hydroxide in accordance with the reaction:

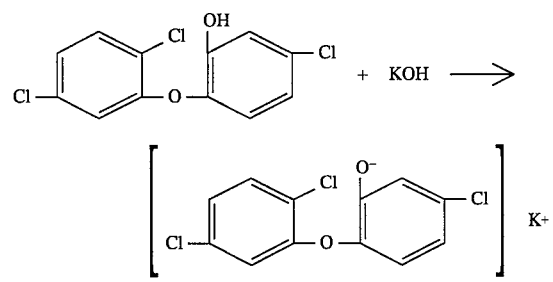

wherein Triclosan is dispersed in a suitable aqueous liquid vehicle at a temperature of about 25° to about 50° C., the pH of the vehicle being adjusted to the alkaline range and preferably a pH of 7.5–9.0.

The proportions of the potassium salt of Triclosan in the composition of the present invention have been characterized as antibacterial proportions thereof, by which it is meant that the proportions of such salt should be sufficient to have the mentioned effect. It is found that at least 0.3% of the potassium salt of Triclosan is desirably present in antibacterial oral compositions although lower percentages are appropriate for mouthwashes.

The potassium salt of Triclosan is compatible with desensitizing potassium salts including potassium nitrate, potassium citrate and potassium oxalate, as well as other active potassium salts such as antitartar salts such as the potassium polyphosphates and particularly potassium pyrophosphate.

The polyphosphates incorporated in the oral compositions of the present invention may be any of various water soluble polyphosphates, including alkali metal pyrophosphates, such as tetrapotassium pyrophosphate, tetrasodium pyrophosphate and with the potassium salts being highly preferred. Instead of the pyrophosphates the tripolyphosphates and other polyphosphates, such as the hexametaphosphates, may be substituted, at least in part. The polyphosphates in compositions of the present invention act to inhibit tartar development on the teeth that are brushed or otherwise treated with the compositions of the present invention.

Generally a concentration of the Triclosan potassium salt in the order of 0.3 to 10% by weight is preferred for toothpastes, dental gels or gel dentifrices and the proportion of anti-tartar polyphosphate is normally within the range of 1 to 10% by weight, preferably being in the range of 1.5 to 4% by weight and more preferably being in the range of 2 to 3% by weight. Desensitizing potassium salts such as potassium nitrate or potassium citrate when present in the oral compositions of the present invention are generally present at a concentration of about 0.5 to about 5% and preferably about 1.0 to about 3%.

Providing that the total proportion of potassium ion in the oral composition is sufficient to provide pain inhibition the sodium analogues of at least some of such compounds, such as tetrasodium pyrophosphate may be present, at least in part. Also, anti-calculus phosphono compounds may be included in the oral compositions, including alkali metal salts of diphosphonic acids and phosphonoalkane carboxylic acid such as azacycloheptane-2,2-diphosphonic acid, phosphonopropane tricarboxylic acid, phosphonobutane-1, 2,4-tricarboxylic acid and ethanehydroxy diphosphonic acid, each alkali metal salt, all preferably as potassium salts.

Another desirable component of the present compositions is a synthetic anionic polymeric polycarboxylate (SAPP), which acts as a stabilizer for the polyphosphate anti-tartar agent when incorporated in the oral compositions of the present invention. The SAPP's employed in the composition of the present invention include water soluble salts of such acids, and very preferably such compounds will be in salt form and the salt will be a potassium salt, which acts to improve the desensitizing effects of the oral compositions of the present invention.

The SAPP-type products are preferably alkali metal salts of polycarboxylates, typically of molecular weights in the 5,000 to 2,000,000 range, preferably 30,000 or 50,000 to 1,100,000 or 1,500,000 and more preferably about 50,000 to 1,100,000. Such SAPP's are preferably 1:4 to 4:1 copolymers of maleic anhydride and/or maleic acid with another polymerizable ethylenically unsaturated monomer, which is preferably methyl vinyl ether. These SAPP's are available commercially under the trademark Gantrez.

Although Gantrez is preferred, also useful in the present oral compositions as SAPP's or as substitutes for them in pan are carboxyvinyl polymers, such as those described in U.S. Pat. Nos. 3,711,604, 3,911,904, 3,919,409, 3,935,3606 and 3,980,767. Such materials are the salts of Carbopols which are polymers of polyacrylic acid crosslinked with minor proportions of polyallyl sucrose or polyallyl pentaerythritol.

The SAPP may be included in the oral compositions of the present invention in the range of 0.5 to 4% by weight preferably 0.8 to 3% by weight and more preferably 1 to 2% by weight.

A water soluble fluoride or source of fluoride ions may be incorporated in the compositions of the present invention. Among the useful sources of fluoride ions are water soluble alkali metal fluorides, such as sodium and potassium fluorides, copper fluorides, such as cuprous fluoride, ammonium fluorosilicate, sodium and ammonium fluorozirconates, sodium and potassium monofluorophosphates and aluminum fluorophosphates (mono-di-and tri-).

When a water soluble fluoride is present, the proportion thereof will usually be that which provides about 100 to 2,300 p.p.m. of fluoride ion (F$^-$) and preferably about 400 to 1,500 p.p.m. of F$^-$ in the composition. Higher proportions, even up to 10,000 p.p.m. of F$^-$, may be used for professional fluoride treatments for anticaries activity.

The orally acceptable vehicle for the oral compositions of the present invention when such compositions are toothpastes, will normally include water, humectant, thickener, surfactant and polishing agent. The water and humectant comprise the liquid portion of the toothpaste. The humectant component of the toothpaste will preferably comprise a mixture of humectants, such as glycerol, sorbitol, and polyethylene glycol, which is most preferred, but other mixtures of humectants and single humectants may also be employed. A normal range of molecular weights for the polyethylene glycol humectants is 200 to 1,000, preferably 400 to 600 or 800, e.g., about 600.

In a toothpaste, the humectant content will generally be in the range of 10 to 50%, preferably 25 to 45% by weight.

Thickeners included in the compositions of the present invention are natural and synthetic gums and colloids such as carrageenan, xanthan gum and sodium carboxymethyl cellulose, as well as gum tragacanth, starch, polyvinylpyrrolidone, hydroxyethyl propylcellulose, hydroxybutyl methyl cellulose, hydroxypropyl methyl cellulose and hydroxyethyl cellulose. Inorganic thickeners, such as colloidal silica, e.g., Syloid 244, and synthetic hectorite, such as Laponite, marketed by Laporte Industries, Ltd, may also be used, and mixtures of such thickeners are also useful. The thickener component of the toothpaste will normally be in the range of 0.2 to 5%, by weight preferably 0.3 to 3% by weight.

A surfactant is also included in the compositions of the present invention. The surfactant will normally be a water soluble detergent, which is useful to clean the teeth and assists the anti-tartar and desensitizing potassium salt components of the oral composition to contact the tooth surfaces and to penetrate into the dentin and pulp, where exposed. The surfactants have useful foaming properties and also aid in producing a uniform toothpaste, in which the active components are evenly distributed. The surfactant is generally anionic, nonionic or ampholytic in nature, and most preferably is anionic. Suitable examples of anionic surfactants are higher alkyl sulfates such as sodium lauryl sulfate and higher fatty acid esters of 1,2 dihydroxy propane sulfonate.

Examples of water soluble nonionic surfactants are condensation products of ethylene oxide with various hydrogen-containing compounds that are reactive therewith and have long hydrophobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., Pluronic materials). Of the mentioned detergents the higher fatty alcohol sulfates are preferred.

Polishing agents which may be incorporated in the oral composition of the present invention include siliceous materials, such as a precipitated amorphous hydrated silica, such as Zeodent 113 or 115, marketed by J. M. Huber Corporation, but other polishing agents may be employed too, including sodium bicarbonate, sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, alumina trihydrate, aluminum silicate, zirconlure silicate, calcined alumina, bentonite, silica gel or colloidal silica, and complex amorphous alkali metal aluminosilicates and mixtures thereof. The content of polishing agent will normally be in the range of 10 to 50% by weight, preferably 15 to 35% by weight and more preferably 15 to 30% by weight.

Various other components of toothpastes may be considered to be additional active materials or adjuvants. Included in this group are: other anti-tartar or anti-calculus compounds, such as zinc chloride, zinc acetate and zinc oxide, and antibacterial agents such as chlorhexidene, cetyl pyridinium chloride and sanguinaria extract; buffers to control pH; tooth whiteners such as hydrogen peroxide, urea peroxide, sodium perborate and calcium peroxide, preservatives; sweeteners, such as potassium (or sodium) saccharin or cyclamate, acesulfam-K, and aspartame; flavors, such as mint (peppermint and spearmint) and menthol; and dyes and pigments, such as chlorophyll and titanium dioxide.

To prepare a toothpaste of a present invention, the humectant is mixed with a thickener, an alkali metal fluoride and an active potassium salt such as potassium nitrate or potassium pyrophosphate and the mixing is continued until the mixture becomes a slurry, which is smooth in appearance. Water is then added and the potassium salt of Triclosan dispersed in an alkaline (pH 7.5–9.0) vehicle is admixed with the slurry. All such mixing is at room temperature, in the range of 20 to 30° C. to prepare a gel phase. Next the gel phase is heated to a temperature in the range of 55° to 75° C., with mixing for 10 to 30 minutes at the elevated temperature.

Although the potassium salt of Triclosan finds use in toothpastes, gels tooth powders, and liquid dentifrices, other oral preparations that are not intended for brushing onto the teeth can also include the potassium salt of Triclosan, and among such products are mouth rinses, antiseptic solutions, chewing gums, tooth treating agents, such as plaque locating solutions, and even dental floss and dental tape. In these non-dentifrice preparations the proportion of the potassium salt of Triclosan will be an antibacterial proportion. The mouth rinses will normally contain water, alcohol, humectant, such as glycerol, sorbitol and/or polyethylene glycol, flavor and sweetener (non-sugar), in addition to the active components mentioned.

The preparation of the oral composition such as a toothpaste wherein the potassium salt of Triclosan is present also includes forming the potassium salt of Triclosan in situ in the composition by dispersing Triclosan in a humectant, adding water to the resulting slurry and mixing potassium hydroxide therewith to a pH in the range of 7.5 to 9 with mixing and continuing the mixing for 10 to 30 minutes after completion of the addition of the potassium hydroxide. Thereafter a dentally acceptable polishing agent is mixed with the slurry for 10 to 30 minutes under a vacuum in the range is 5 to 50 millimeters of mercury to produce a paste or gel, an anionic detergent is mixed with the resulting paste or gel and then mixing is continued for 3 to 10 minutes under a vacuum in the range of 5 to 50 mm of mercury.

In the foregoing process, after the addition of potassium hydroxide to produce the salt the paste is heated to a temperature in the range of 55° to 75° C. with mixing which is continued for 10 to 30 minutes. The gel phase that is obtained is cooled.

To make mouthwashes or other liquid preparations the main active components may be dissolved or dispersed in an appropriate liquid medium usually an aqueous alcoholic medium and polymeric and abrasive or water insoluble materials will normally be omitted.

The following Example is given to illustrate the invention and is not to be considered as limiting the scope of the claims. Unless otherwise indicated all parts and percentages are by weight and all temperatures are in ° C.

| Toothpase Formula | |
|---|---|
| Component | Percent |
| Glycerol | 10.00 |
| Polyethylene glycol 600 | 3.00 |
| Carrageenan | 1.00 |
| Sodium saccharin | 0.50 |
| Sodium fluoride | 0.25 |
| Titanium dioxide | 0.50 |
| Tetrapotassium pyrophosphate | 2.50 |
| Triclosan potassium salt | 2.00 |
| Water | 28.50 |
| Sorbitol solution (70% aqueous solution) | 25.00 |
| Silica (precipitated amorphous hydrated silicon dioxide) | 25.00 |
| Sodium lauryl sulfate | 1.50 |
| Peppermint flavor | 1.00 |
| | 100.00 |

A toothpaste of the above formula is made by first dissolving and/or dispersing carrageenan, sodium saccharin, sodium fluoride, tetrapotassium pyrophosphate and titanium dioxide in a solution of the polyethylene glycol 600 in glycerol at room temperature and admixed until the appearance of the mixture is smooth. Sorbitol and water are then admixed with the smooth slurry after which the potassium salt of Triclosan is added thereto. A gel phase intermediate product is obtained is which is then heated to about 65° C. Silica is added to the cooled gel phase and admixed therewith under full vacuum (about 30 mm. of Hg) after which sodium lauryl sulfate and flavor are admixed therewith and mixing is continued under such vacuum.

The toothpaste prepared in accordance with the above procedure is effective for plaque and tartar control as well as for reducing tooth pain and sensitivity. Upon storage little or no separation of the Triclosan salt is observed.

Oral compositions other than toothpastes may also be made by employing the required components of the invention in a liquid medium, to make a mouthwash. In one such product the mouthwash base or solvent system will be 20% of ethanol in water, and will contain about 1/10 of each of the percentages of Triclosan salt and potassium pyrophosphate in the toothpaste of Example. In another product the mouthwash will also contain about 0.05% or 0.08% of sodium or potassium fluoride.

The invention has been described in conjunction with illustrative embodiments thereof but is not to be considered to be limited to these because one of skill in the art will be able to utilize substitutes and equivalents thereof without departing from the bounds of the invention and the spirit thereof.

I claim:

1. An aqueous based oral composition which comprises an orally acceptable vehicle for such composition and the potassium salt of 2,4,4'-trichloro-2'-hydroxydiphenyl ether (Triclosan) as the sole antibacterial agent.

2. The oral composition according to claim 1 wherein the potassium salt of Triclosan is present in amount of 0.5 to 4% by weight.

3. An aqueous based oral composition which comprises an orally acceptable vehicle for such composition and the potassium salt of 2,4,4'-trichloro-2'-hydroxydiphenyl ether (Triclosan), and an alkali metal salt, the Triclosan salt having improved compatibility with the alkali metal salt in the composition.

4. The oral composition of claim 1 wherein there is incorporated in the composition an effective antitartar amount of potassium pyrophosphate.

5. The oral composition of claim 1 wherein there is incorporated in the composition an effective tooth desensitization amount of potassium nitrate.

6. A method for reducing the formation of plaque on teeth which comprises applying to said teeth the composition according to claim 1.

* * * * *